United States Patent [19]
Luce

[11] Patent Number: 6,159,148
[45] Date of Patent: Dec. 12, 2000

[54] NON-CONTACT TONOMETER HAVING NON-LINEAR PRESSURE RAMP

[75] Inventor: David A. Luce, Clarence Center, N.Y.

[73] Assignee: Leica Microsystems Inc., Depew, N.Y.

[21] Appl. No.: 09/114,698

[22] Filed: Jul. 13, 1998

[51] Int. Cl.[7] .................................................. A61B 3/16
[52] U.S. Cl. ........................................................ 600/405
[58] Field of Search ................................... 600/405, 558, 600/401

[56] References Cited

U.S. PATENT DOCUMENTS

| | | |
|---|---|---|
| 4,996,990 | 3/1991 | Hideshima . |
| 5,002,056 | 3/1991 | Takahashi et al. ................ 600/405 |

*Primary Examiner*—Cary O'Connor
*Assistant Examiner*—Pamela Wingood
*Attorney, Agent, or Firm*—Simpson, Simpson & Snyder, L.L.P.

[57] ABSTRACT

A non-contact tonometer having a fluid pulse generating system for causing corneal applanation is improved by changing the pressure versus time characteristics of the fluid pulse from a linearly increasing relationship of the prior art to a non-linearly increasing relationship which reduces the impulse energy delivered to the eye during testing for purposes of patient comfort. In a preferred embodiment, an automatically driven piston for producing an air pulse is provided with a linearly increasing current source for driving the piston mechanism, whereby the pressure ramp of the air pulse increases as a squared function of time to reduce impulse energy delivered to the eye.

6 Claims, 6 Drawing Sheets

NON-CONTACT TONOMETER HAVING NON-LINEAR PRESSURE RAMP

BACKGROUND

A. Field of the Invention

The present invention relates generally to the field of non-contact tonometry, and more particularly to a non-contact tonometer having a non-linear pressure ramp during fluid pulse generation for increasing patient comfort.

B. Description of the Prior Art

In the operation of known non-contact tonometers for measuring intraocular pressure (IOP) of a patient's eye, an increasing force fluid pulse is discharged through a tube aimed at the eye to deform the cornea from a state of convexity, through an instantaneous state of "applanation" wherein a predetermined area of the cornea is flattened, to a state of concavity; the cornea is then allowed to return to its original convex state under natural forces. Opto-electronic means are used to continuously monitor the corneal deformation and thereby determine the moment of applanation. As shown in PRIOR ART FIG. 1, the fluid pulse is commonly generated by a piston momentarily driven by a rotary solenoid to rapidly compress air within a plenum chamber, thereby forcing air from a discharge tube in communication with the plenum chamber.

Before the introduction of small, low-priced pressure transducers capable of quickly and accurately sensing fluid pressure within the plenum chamber, the time interval required to achieve applanation was recorded and used as a correlate to IOP. Intuitively, the longer the eye had to be subjected to an increasing force fluid pulse in order to flatten the cornea, the higher the patient's IOP was. A solenoid was employed to drive the piston because energizing the solenoid coil with a constant current supply as indicated in FIG. 2 resulted in a linearly increasing pressure ramp as depicted in FIG. 3. This follows from the fact that plenum pressure is proportional to the piston velocity, and the piston velocity is proportional to the first time integal of the current supplied to the solenoid coil. Thus, a linearly increasing pressure ramp has in the past allowed for reasonably accurate calculation of IOP based on a measurement of elapsed time necessary to achieve applanation.

As pressure sensor technology became more sophisticated, non-contact tonometers included pressure transducers to measure plenum pressure directly, offering improved accuracy. Although this improvement has obviated the need for the linearly increasing pressure ramp used in older non-contact tonometers, manufacturers continue to rely exclusively on constant current for energizing the drive means to produce a fluid pulse. A recognized, but heretofore accepted, drawback of using a constant current source is the system discontinuity related to the abrupt increase in driving current from zero to its constant value, as seen in FIG. 2. Such discontinuity has dictated that a high voltage power supply be used in the instrument to provide the initial rapid rise in current, and has resulted in mechanical oscillations in the fluid pulse system.

Since the fluid pulse directed at the eye is a source of patient discomfort, and since this in turn may affect test results, an ongoing goal of those who design and manufacture non-contact tonometers has been to make the test procedure more comfortable for the patient being tested. Heretofore, efforts to improve patient comfort have been directed primarily at stopping fluid pulse generation as early as possible while nevertheless ensuring that applanation of the cornea is achieved. Examples of this approach may be found in commonly-owned U.S. patent application Ser. No. 08/659,704, now U.S. Pat. No. 5,779,633, and also in U.S. Pat. No. 5,279,300 assigned to Nidek Co., Ltd. Such prior art advancements have not involved changes in the linear nature of the fluid pulse pressure ramp.

SUMMARY OF THE INVENTION

It is a primary object of the present invention to make the IOP measurement procedure more comfortable for patients tested by a non-contact tonometer which directs a fluid pulse at the eye.

It is another object of the present invention to provide a non-contact tonometer having a measurement uncertainty range which is a substantially constant percentage of the measured IOP.

These objects are achieved in a novel manner in a preferred embodiment by altering the nature of the fluid pulse pressure ramp from one which increases linearly with time, as is known in the prior art, to one which increases as a squared function of time. This alteration of the fluid pulse pressure ramp is preferably achieved by using a linearly increasing current source, rather than a constant current source, to energize a drive means, i.e. a solenoid, operably connected to a fluid compression means such as a piston. The rate of increase in the energizing current is selected to provide a non-linear pressure ramp which results in less impulse energy being delivered to a patient's eye for a large majority of the population as compared with instruments of the prior art.

BRIEF DESCRIPTION OF THE DRAWINGS

The nature and mode of operation of the present invention will now be more fully described in the following detailed description of the preferred embodiments taken with the accompanying drawing figures, in which.

DETAILED DESCRIPTION OF THE PREFERRED EMBODIMENTS

Figure 4:
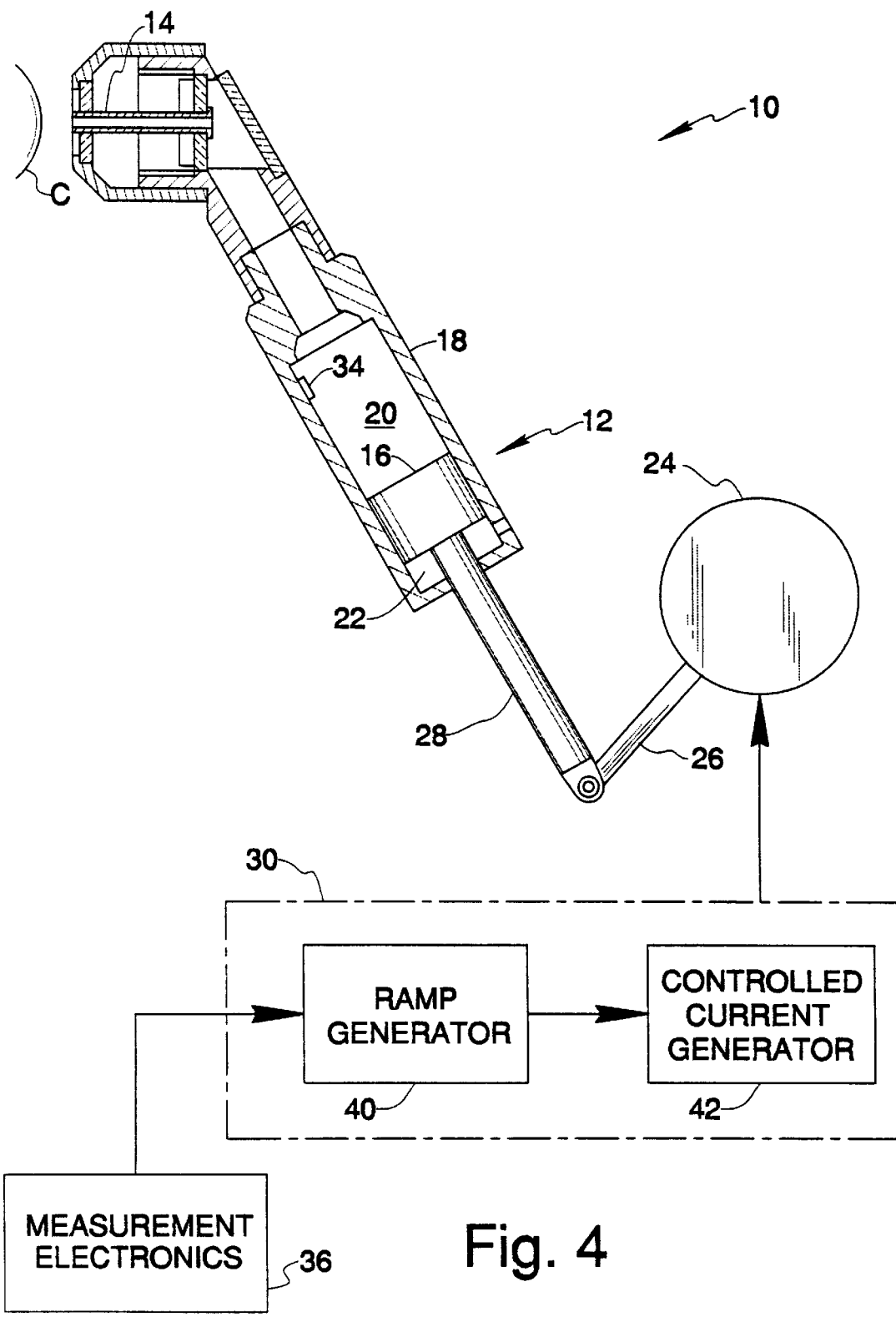
FIG. 4 is a schematic diagram, similar to that of FIG. 1, however showing a non-contact tonometer formed in accordance with the present invention.
Figure 5:
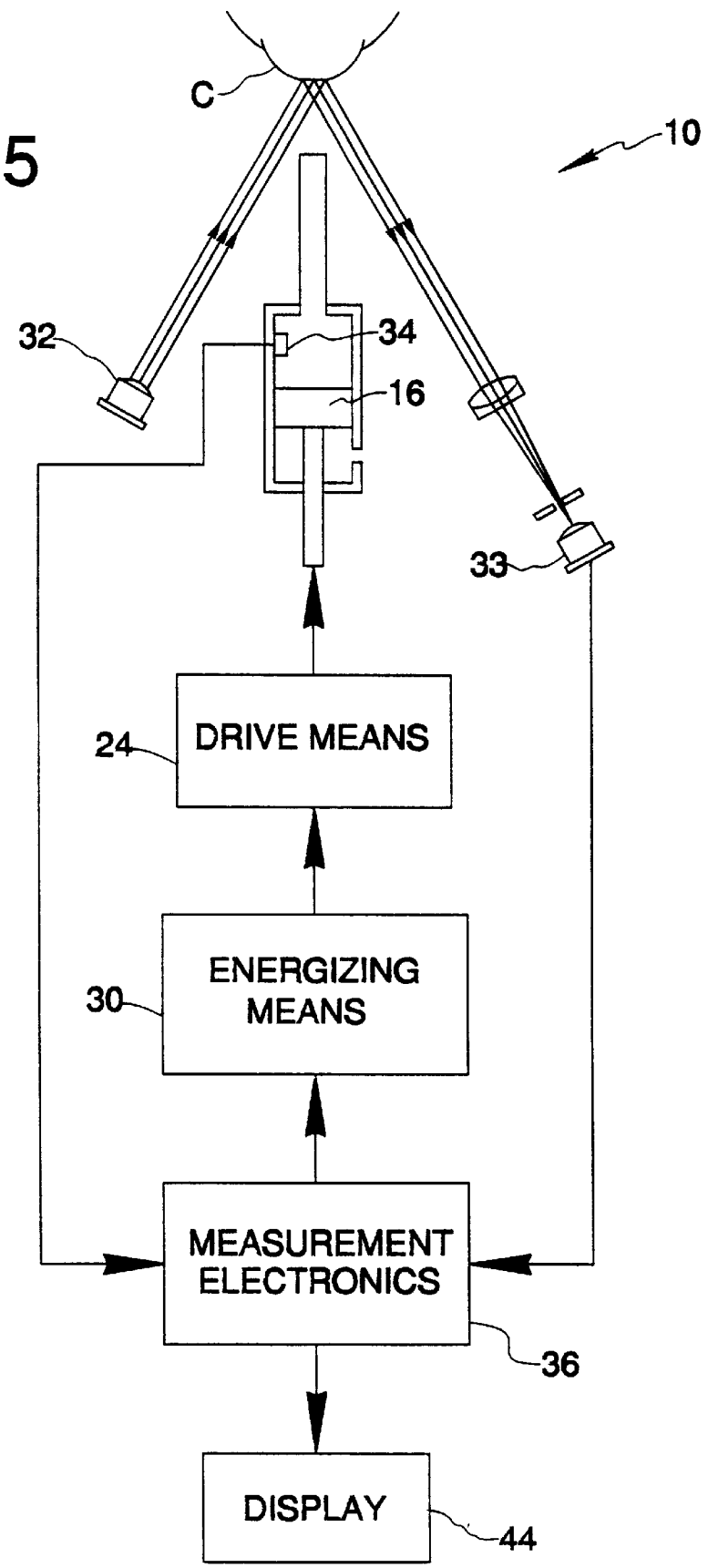
FIG. 5 is another schematic diagram of a non-contact tonometer formed in accordance with the present invention.

Referring now to FIGS. 4 and 5, a non-contact tonometer generally designated by the reference numeral 10 is shown schematically as including a fluid compression means 12 arranged in flow communication with a fluid discharge tube 14 aligned in a test position for directing a pulse of air at a patient's eye to cause deformation of cornea C. Compression means 12 includes a piston 16 cooperating with a cylinder 18 to define respective first and second plenum chambers 20 and 22. A rotary solenoid 24 is provided for automatically driving compression means 12 to generate an air pulse, and includes a moving armature 26 pivotally linked to an end of piston rod 28. When the solenoid coil (not shown) is energized by a current source 30, armature 26 rotates in a clockwise direction, as shown in FIG. 4, to move piston 16 in a generally upward direction to rapidly decrease the volume of the first plenum chamber 20, causing an air pulse to be discharged from fluid discharge tube 14. Of course, other automatic drive means may be employed to move the piston, for example a linear motor.

As in PRIOR ART non-contact tonometers, measurement means are provided for detecting corneal applanation and determining IOP. The progressive deformation of cornea C is monitored by an opto-electronic system such as that currently found in the XPERT NCT manufactured by Leica Microsystems Inc. FIG. 5 illustrates one possible opto-electronic system which includes an emitter 32 for directing an obliquely incident beam of light to cornea C and a photosensitive detector 33 arranged to receive corneally reflected rays. The corneally reflected rays, which are normally "fanned out" or dispersed by the curved surface of the cornea C, become concentrated in the direction of detector 33 as the surface of cornea C is flattened by a fluid pulse, whereby detector 33 generates a peak signal indicating the occurrence of corneal applanation. An opto-electronic applanation detection system as taught by commonly-owned U.S. patent application Ser. No. 09/054,723, now U.S. Pat. No. 5,954,645, is another possible system for monitoring corneal deformation. As a further aspect of the measurement means, pressure within plenum chamber 20 is preferably measured by a pressure transducer 34. Signals derived from detector 33 and pressure transducer 34 are processed and evaluated by measurement electronics 36 to determine measured IOP, which is reported by a display 44 or the like.

Figure 1:
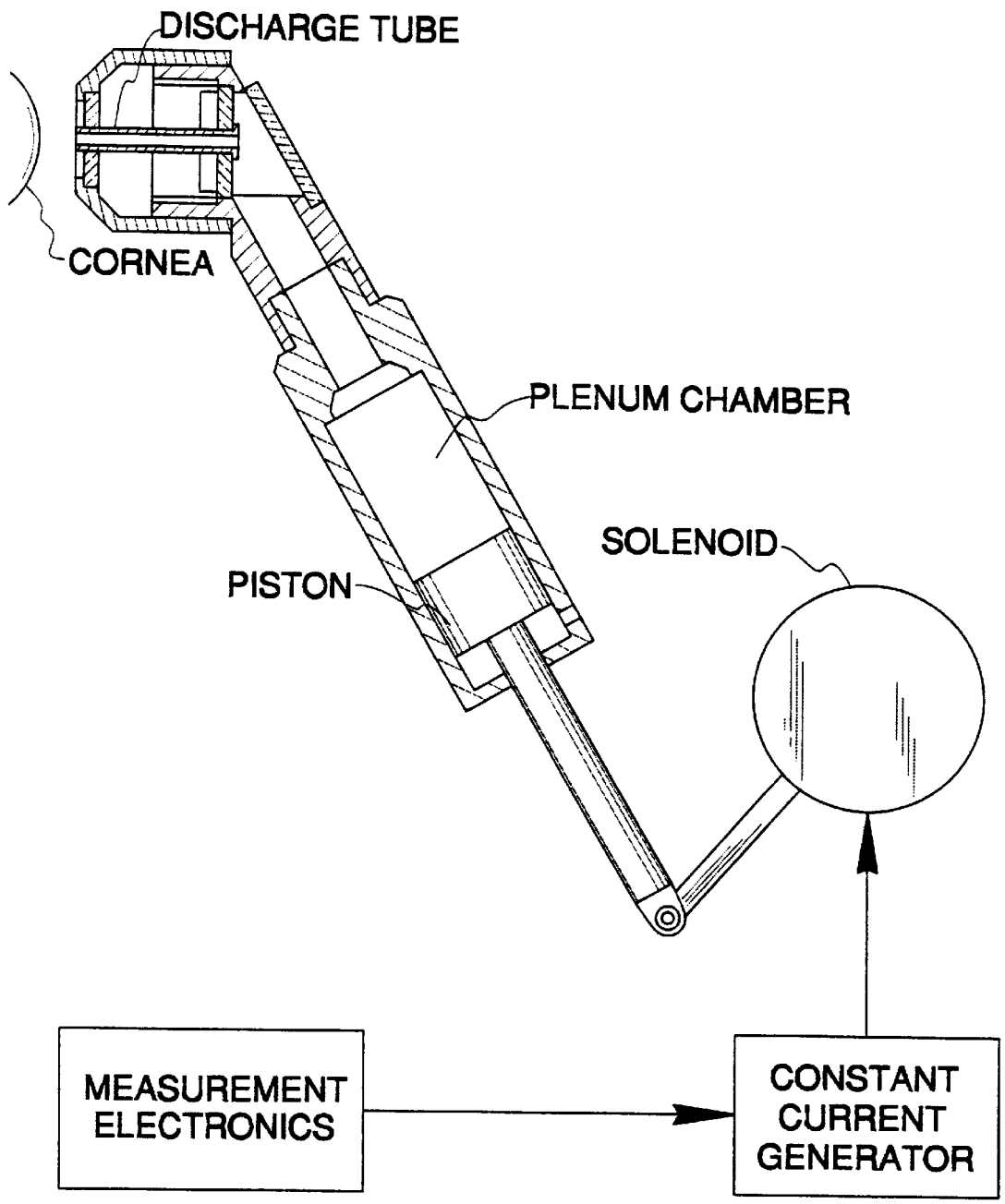
FIG. 1 is a schematic diagram of a PRIOR ART non-contact tonometer, illustrating a fluid pulse system thereof.
Figure 2:
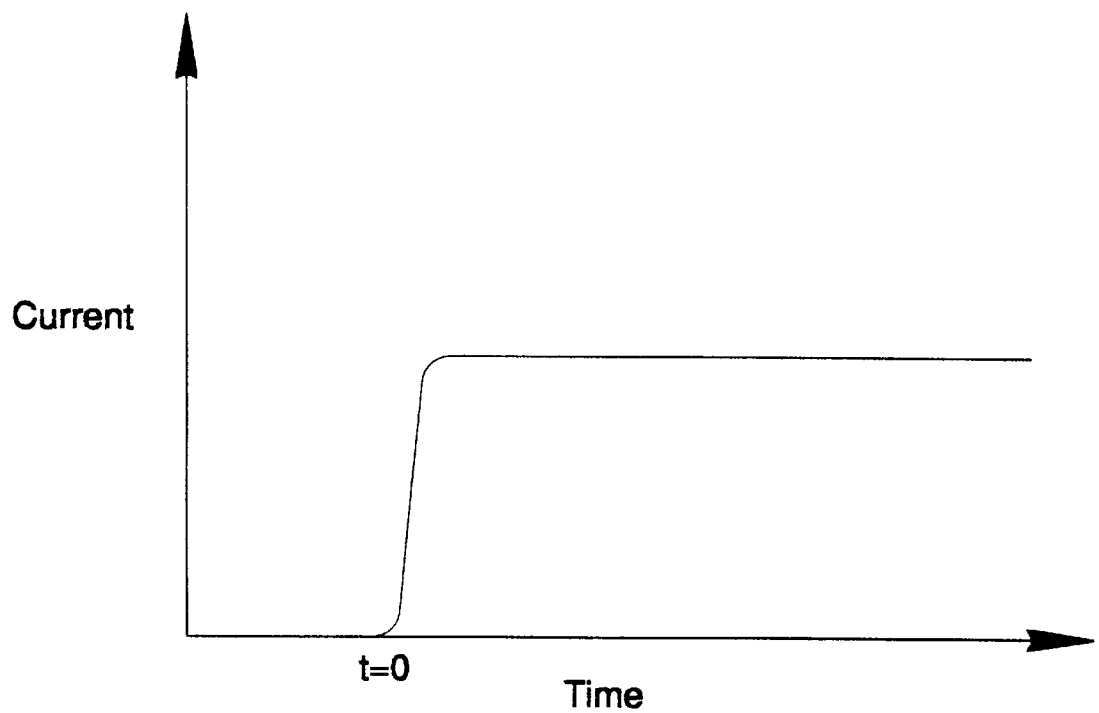
FIG. 2 is a plot of solenoid driving current as a function of time in a PRIOR ART non-contact tonometer.
Figure 3:
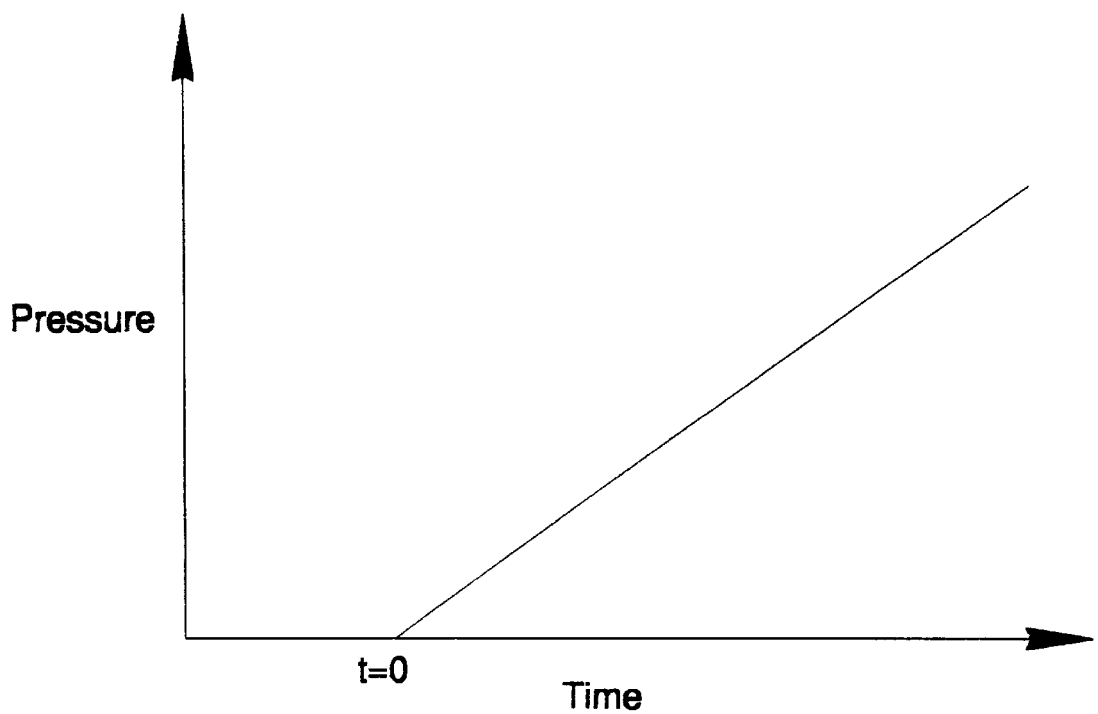
FIG. 3 is a plot of plenum pressure as a function of time in a PRIOR ART non-contact tonometer.

Non-contact tonometer 10 of FIGS. 4 and 5 differs from the PRIOR ART non-contact tonometer depicted in FIG. 1 with respect to the nature of energizing means 30 supplying current to rotary solenoid 24 (or other automatic drive means) to move piston 16. In particular, the present invention utilizes a current source which increases the current delivered to solenoid 24 as a function of time, such that the force moving piston 16 increases as a corresponding function of time. As mentioned above in the Background of the Invention, non-contact tonometers have previously used a constant current source to energize the automatic drive means of the instrument.

Figure 6:
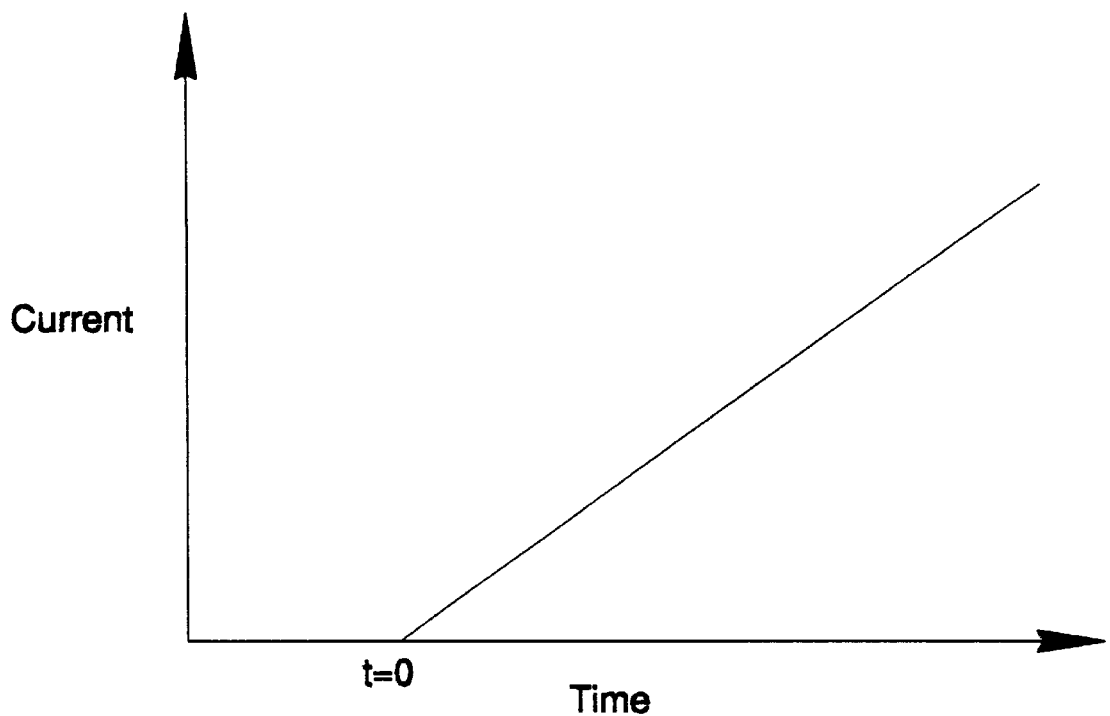
FIG. 6 is a plot similar to that of FIG. 2, however showing solenoid driving current as a function of time in a non-contact tonometer formed in accordance with the present invention.

As shown in block diagram in FIG. 4, energizing means 30 includes a ramp generator circuit 40 connected to a current generator circuit 42 for supplying current to solenoid 24 under the control of measurement electronics 36. Ramp generator circuit 40 supplies a linearly increasing voltage across voltage controlled current generator circuit 42, which in turn supplies linearly increasing current to solenoid 24, as depicted graphically in FIG. 6. The consequences of using a linearly increasing current source to energize solenoid 24, as opposed to using a constant current source, become apparent from an overview of the physical equations describing the air pulse system.

Since the force driving piston 16 is proportional to the current energizing solenoid 24, we have $$F_P = K_1 i$$

where $F_P$ is the piston driving force, $K_1$ is a first proportionality constant, and i is the current. Stated another way, $$m_P a_P = K_1 i$$

where $m_P$ is the piston mass and $a_P$ is the piston acceleration. Thus $$\frac{dv_P}{dt} = \frac{K_1}{m_P} i$$

here $v_P$ is the piston velocity and t is time. Because the current varies linearly with time, the above equation may be rewritten $$\frac{dv_P}{dt} = \frac{K_1}{m_P} \alpha t$$

where $\alpha$ is a scaling constant (slope) for the current ramp representing the rate of change of driving current. Integrating yields the following expression:

$$v_P = \frac{K_1}{2m_P} \alpha t^2$$

in which the piston velocity is expressed as a squared function of time. Based on fluid mechanics of the system, the force delivered to cornea C is approximately proportional to the piston velocity, whereby $$F_{eye} = K_2 v_P$$

in which $K_2$ is a second proportionality constant. Consequently, by substitution, $$F_{eye} = \frac{K_1 K_2}{2m_P} \alpha t^2$$

such that the force delivered to cornea C to cause applanation increases as a squared function of time. Likewise the plenum pressure, which is preferably measured by pressure sensor 34 and correlated with IOP, also increases as a squared function of time.

Figure 7:
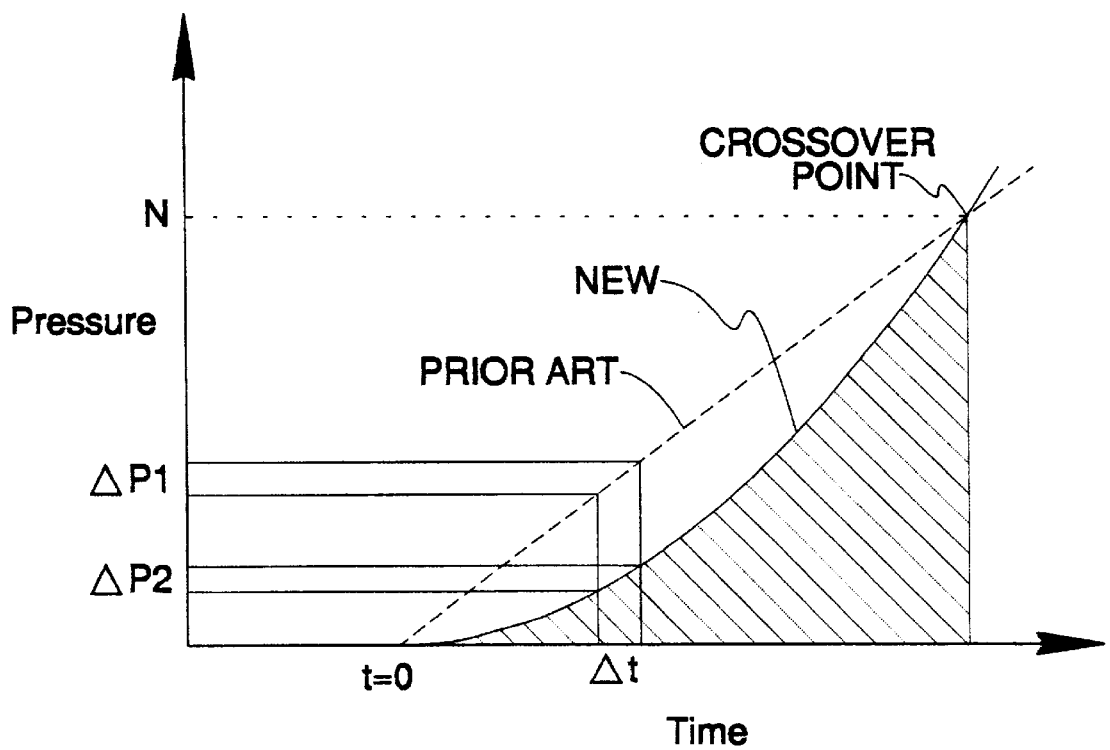
FIG. 7 is a plot similar to that of FIG. 3, however additionally showing plenum pressure as a function of time in a non-contact tonometer formed in accordance with the present invention.

The difference, from the patient's standpoint, involves the rate effect of neural response in the patient's eye. In FIG. 7, which offers a comparison of a non-linear pressure ramp of the present invention with a linear pressure ramp of the prior art, the impulse delivered to the eye is proportional to the area under the pressure-time curve. It is readily apparent that for tests where measured IOP is a certain value N, and both the prior art pressure ramp and a non-linear pressure ramp according to the present invention achieve applanation at the same time (the "crossover point"), the hatched area under the non-linear pressure-time curve will be less than the area under the linear pressure-time curve. Consequently, for a patient having the specified IOP value corresponding to the crossover point pressure N, the uncomfortable sensation caused by the air pulse will be reduced by the present invention.

Figure 8:
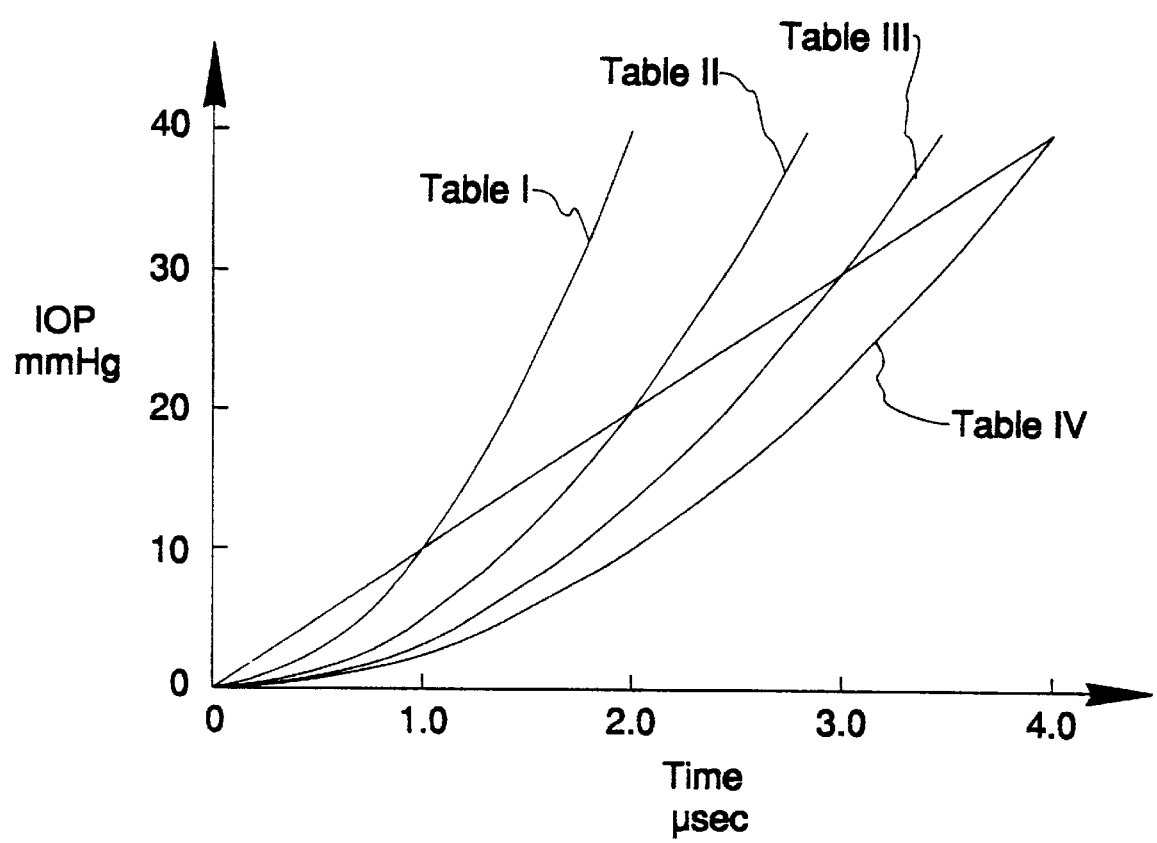
FIG. 8 is a plot of IOP as a function of time for a several groups of trial measurements, wherein the rate of increase of energizing current was different for each group.

Since a goal of the present invention is to make the IOP measurement procedure more comfortable for the majority of patients tested, the crossover point at which the non-linear pressure ramp crosses a linear pressure ramp of the prior art is chosen to occur at the pressure corresponding to the average population IOP, which is about 15 mmHg, within a time interval of about two milliseconds. At this crossover point, both a prior art non-contact tonometer and a non-contact tonometer according to the present invention will have delivered an air pulse sufficient to cause corneal applanation in the same period of time; however, the impulse felt by the patient will be significantly less with the instrument of this invention. The crossover point may be controlled by suitably selecting the rate of increase $\alpha$ of the driving current. FIG. 8, based on Tables I through IV below, shows the effect of varying $\alpha$ on the shape of the non-linear pressure ramp and the crossover point.

Tables I–IV each offer a comparison of pressure ramp data for a prior art non-contact tonometer using a constant current source whereby the measured IOP equals 10 t, and a new non-contact tonometer using a ramped current source whereby the measured IOP equals $K_{sys}\alpha t^2$, with $K_{sys}$ representing a system constant for the particular air pulse mechanism. The designations $t_1$ and $t_2$ denote time in milliseconds for prior art and new non-contact tonometers, respectively, while $A_1$ and $A_2$ refer to areas under the prior art and new pressure-time curves, respectively. The crossover point is highlighted in each table.

In Table I, the value of $\alpha$ is chosen such that $K_{sys}\alpha$ is equal to 10.00.

TABLE I

| $K_{sys}\alpha$ | $t_1$ | $t_2$ | IOP (mmHg) | $A_1$ | $A_2$ | $R = A_2/A_1$ |
|---|---|---|---|---|---|---|
| 10.00 | 0.44 | 0.66 | 4.40 | 0.97 | 0.96 | 0.99 |
| 10.00 | 0.50 | 0.71 | 5.00 | 1.25 | 1.18 | 0.94 |
| 10.00 | 1.00 | 1.00 | 10.00 | 5.00 | 3.33 | 0.67 |
| 10.00 | 2.00 | 1.41 | 20.00 | 20.00 | 9.43 | 0.47 |
| 10.00 | 3.00 | 1.73 | 30.00 | 45.00 | 17.32 | 0.38 |
| 10.00 | 4.00 | 2.00 | 40.00 | 80.00 | 26.67 | 0.33 |

Table II is a second comparison of pressure ramp data similar to the comparison presented in Table I, however the value of $\alpha$ is chosen such that $K_{sys}\alpha$ equals 5.00.

TABLE II

| $K_{sys}\alpha$ | $t_1$ | $t_2$ | IOP (mmHg) | $A_1$ | $A_2$ | $R = A_2/A_1$ |
|---|---|---|---|---|---|---|
| 5.00 | 0.50 | 1.00 | 5.00 | 1.25 | 1.67 | 1.33 |
| 5.00 | 0.89 | 1.33 | 8.90 | 3.96 | 3.96 | 1.00 |
| 5.00 | 1.00 | 1.41 | 10.00 | 5.00 | 4.71 | 0.94 |
| 5.00 | 2.00 | 2.00 | 20.00 | 20.00 | 13.33 | 0.67 |
| 5.00 | 3.00 | 2.45 | 30.00 | 45.00 | 24.49 | 0.54 |
| 5.00 | 4.00 | 2.83 | 40.00 | 80.00 | 37.71 | 0.47 |

Table III is a third comparison of pressure ramp data similar to the comparisons presented in Tables I and II, but the value of $\alpha$ is chosen so that $K_{sys}\alpha$ equals 3.33.

TABLE III

| $K_{sys}\alpha$ | $t_1$ | $t_2$ | IOP (mmHg) | $A_1$ | $A_2$ | $R = A_2/A_1$ |
|---|---|---|---|---|---|---|
| 3.33 | 0.50 | 1.23 | 5.00 | 1.25 | 2.04 | 1.63 |
| 3.33 | 1.00 | 1.73 | 10.00 | 5.00 | 5.78 | 1.16 |
| 3.33 | 2.00 | 2.45 | 20.00 | 20.00 | 16.34 | 0.82 |
| 3.33 | 3.00 | 3.00 | 30.00 | 45.00 | 30.02 | 0.67 |
| 3.33 | 4.00 | 3.47 | 40.00 | 80.00 | 46.21 | 0.58 |

Finally, Table IV is a fourth comparison of pressure ramp data similar to the comparisons presented in Tables I through III, however the value of $\alpha$ is chosen such that $K_{sys}\alpha$ is equal to 2.50.

TABLE IV

| $K_{sys}\alpha$ | $t_1$ | $t_2$ | IOP (mmHg) | $A_1$ | $A_2$ | $R = A_2/A_1$ |
|---|---|---|---|---|---|---|
| 2.50 | 0.50 | 1.41 | 5.00 | 1.25 | 2.36 | 1.89 |
| 2.50 | 1.00 | 2.00 | 10.00 | 5.00 | 6.67 | 1.33 |
| 2.50 | 2.00 | 2.83 | 20.00 | 20.00 | 18.86 | 0.94 |
| 2.50 | 3.00 | 3.46 | 30.00 | 45.00 | 34.64 | 0.77 |
| 2.50 | 4.00 | 4.00 | 40.00 | 80.00 | 53.33 | 0.67 |

It will be understood from the above tables and from FIG. 8 that decreasing $\alpha$ increases the crossover point IOP. More importantly, a one-third reduction in area under the non-linear pressure-time curve is realized at each of the four crossover point limits listed above. Accordingly, the present invention offers a significant decrease in impulse delivered to the eye for a majority of the population having an IOP near the population average, thereby improving patient comfort during testing. This has the added benefit of reducing the incidence of false readings due to blinking.

Another consequence of using a non-linear pressure ramp relates to measurement accuracy. Attention is directed again to FIG. 7. For a given uncertainty $\Delta t$ in time t, the instrument of the PRIOR ART is subject to a corresponding uncertainty $\Delta P_1$ in measured IOP which remains constant regardless of the measured IOP. Thus, when measurement error is expressed as a percentage of the absolute IOP reading, such error will be greater for lower values of measured IOP and vice versa. By contrast, for the same degree of uncertainty $\Delta t$ in time t, the instrument of the present invention is subject to a corresponding uncertainty $\Delta P_2$ in measured IOP which varies with measured IOP and is essentially a constant percentage of measured IOP.

Finally, the preferred embodiment of the present invention advantageously eliminates the aforementioned system discontinuity found in the prior art by allowing the driving current to increase at a constant rate during air pulse generation.

While the above description is directed to the use of a linearly ramped current source resulting in a "time squared" non-linear pressure ramp, it will be recognized by those skilled in the art that other current source functions may be employed in order to obtain a non-linear pressure ramp allowing similar benefits as described herein. It will also be recognized that a non-linear pressure ramp may be achieved by means for controlling air pressure within plenum chamber 20 other than means varying the piston driving current, such as by providing a specialized valve for regulating flow through the discharge tube. Therefore, the claims should not be construed as being limited to the use of a linearly ramped current source according to the preferred embodiment where no such limitation is stated.

What is claimed is:

1. A non-contact tonometer for measuring IOP of an eye, said non-contact tonometer comprising:
   compression means for generating a fluid pulse to cause applanation of a cornea at which said fluid pulse is directed;
   automatic drive means operably connected to said compression means for moving said compression means to generate said fluid pulse;
   energizing means connected to said drive means for supplying current to said drive means in order to move said compression means, wherein said current increases as a function of time such that fluid pressure in said compression means increases substantially as a squared function of time; and measurement means for detecting said corneal applanation and determining said IOP.

2. The non-contact tonometer according to claim 1, wherein said compression means includes a piston, said automatic drive means includes a solenoid, and said energizing means includes a ramped current driver supplying current to said solenoid.

3. The non-contact tonometer according to claim 1, wherein said squared function of time is scaled so that said fluid pulse causes applanation within a predetermined time interval in an eye having a population average IOP.

4. The non-contact tonometer according to claim 1, wherein said measurement means includes a pressure sensor for generating a first signal representative of a plenum pressure of said compression means, an opto-electronic system for monitoring said cornea and generating a second signal indicating said time corresponding to said corneal applanation, and evaluation means for processing said first and second signals to determine said IOP.

5. A non-contact tonometer for measuring IOP of an eye, said non-contact tonometer comprising:

a driven compression means for generating a fluid pulse to cause applanation of a cornea at which said fluid pulse is directed;

means connected to said compression means for controlling the fluid pressure in said compression means such that said fluid pressure increases as a non-linear function of time during generation of said fluid pulse; and measurement means for detecting said corneal applanation and determining said IOP.

6. The non-contact tonometer according to claim 5, wherein said non-linear function of time is scaled so that said fluid pulse causes applanation within a predetermined time interval in an eye having a population average IOP.

* * * * *